United States Patent
Dekker et al.

(10) Patent No.: US 8,784,367 B2
(45) Date of Patent: Jul. 22, 2014

(54) SENSOR AND CONTROL UNIT FOR FLOW CONTROL AND A METHOD FOR CONTROLLED DELIVERY OF FLUID

(75) Inventors: Ronald Dekker, Eindhoven (NL); Jaap Haartsen, Eindhoven (NL); Pascal De Graaf, Eindhoven (NL); Antoon Marie Henrie Tombeur, Lommel (BE); Adrianus Johannes Maria Van Tuijl, Nijmegen (NL)

(73) Assignee: Koninklijke Philips N.V, Eindhoven (NL)

( * ) Notice: Subject to any disclaimer, the term of this patent is extended or adjusted under 35 U.S.C. 154(b) by 561 days.

(21) Appl. No.: 13/001,798

(22) PCT Filed: Jul. 2, 2009

(86) PCT No.: PCT/IB2009/052874
§ 371 (c)(1),
(2), (4) Date: Dec. 29, 2010

(87) PCT Pub. No.: WO2010/004484
PCT Pub. Date: Jan. 14, 2010

(65) Prior Publication Data
US 2011/0118705 A1  May 19, 2011

(30) Foreign Application Priority Data
Jul. 8, 2008 (EP) ..................... 08159864

(51) Int. Cl.
*A61M 31/00* (2006.01)
*G01F 1/68* (2006.01)

(52) U.S. Cl.
USPC .............. 604/65; 73/204.23; 604/66; 604/67; 604/890.1

(58) Field of Classification Search
USPC ........ 604/65–68, 890.01; 73/204.23; 600/476
See application file for complete search history.

(56) References Cited

U.S. PATENT DOCUMENTS

| 5,533,412 A | 7/1996 | Jerman et al. |
| 5,569,187 A | 10/1996 | Kaiser |

(Continued)

FOREIGN PATENT DOCUMENTS

| EP | 1065475 A2 | 1/2001 |
| EP | 1840535 A1 | 10/2007 |

(Continued)

OTHER PUBLICATIONS

Dekker et al: "Substrate Tranfer for RF Technologies"; IEEE Transactions on Electron Devices, Mar. 2003, vol. 50, No. 3, pp. 747-757.

(Continued)

*Primary Examiner* — Kami A Bosworth
*Assistant Examiner* — Imani Hayman

(57) ABSTRACT

The invention relates to a sensor (102) and a control unit (702) for cooperation with the sensor. The sensor (102) serves for measuring a velocity of a fluid (308) flowing through a channel (306). The sensor (102) employs a thermal measuring principle, which measuring principle is robust regarding disturbances on the amount of power dissipated by the heating element (106). A sensor receiver (110) is arranged for receiving an electromagnetic radiation generated by a control transmitter (722) comprised in a control (702) unit for cooperation with the sensor (102). The electromagnetic radiation is employed for powering the heating element (106) which is arranged for heating the fluid. On the basis of a measurement signal generated by a transducer arrangement comprised in the sensor (102), a control actuator (724) controls the velocity of the fluid. For this purpose a sensor transmitter (116) is arranged for transmitting the measurement signal to a control receiver (734).

20 Claims, 5 Drawing Sheets

(56) References Cited

U.S. PATENT DOCUMENTS

| | | | |
|---|---|---|---|
| 5,704,352 | A | 1/1998 | Tremblay et al. |
| 6,589,229 | B1 | 7/2003 | Connelly et al. |
| 6,685,668 | B1 | 2/2004 | Cho et al. |
| 7,082,843 | B2 | 8/2006 | Clark et al. |
| 7,096,729 | B2 | 8/2006 | Repko et al. |
| 2003/0115952 | A1 | 6/2003 | Mayer et al. |
| 2004/0215067 | A1 | 10/2004 | Stiger et al. |
| 2005/0059926 | A1 | 3/2005 | Sage, Jr. et al. |
| 2005/0277839 | A1 | 12/2005 | Alderman et al. |
| 2006/0142692 | A1 | 6/2006 | Jacobson et al. |
| 2007/0179448 | A1 | 8/2007 | Lim et al. |
| 2007/0191690 | A1 | 8/2007 | Hasse et al. |

FOREIGN PATENT DOCUMENTS

| | | |
|---|---|---|
| JP | 05-329119 | 12/1993 |
| WO | 0120269 A1 | 3/2001 |
| WO | 03071384 A2 | 8/2003 |

OTHER PUBLICATIONS

Dekker et al: "A 10 um Thick RF-ID Tag for Chip-In-Paper Applications"; IEEE BCTM 2.1, 2005, pp. 18-21.

SENSOR AND CONTROL UNIT FOR FLOW CONTROL AND A METHOD FOR CONTROLLED DELIVERY OF FLUID

FIELD OF THE INVENTION

The invention relates to a sensor for measuring a velocity of a fluid flowing through a channel.

The invention further relates to a control unit for cooperation with the sensor.

Furthermore, the invention relates to a system comprising the sensor and the control unit.

The invention further relates to use of the system in a medical application.

Moreover, the invention relates to a method for delivery of a liquid medication.

BACKGROUND OF THE INVENTION

In U.S. Pat. No. 5,533,412, a fluid flow meter is disclosed, comprising a conduit for flow of a fluid, a heating element being inside the conduit for generating a thermal pulse in the fluid and two-spaced apart sensors being inside the conduit and positioned downstream of the heating element, wherein the fluid carries a thermal pulse through the conduit to the two spaced apart sensors and wherein a transit time of the thermal pulse between the spaced apart sensors measures a fluid flow velocity. The fluid flow meter furthermore comprises circuitry being attached to the conduit for providing the heating element with a power pulse.

The techniques disclosed in U.S. Pat. No. 5,533,412 are not suitable for applications in which a channel is regularly replaced, for instance medical applications performed in sterile conditions such as intravenous infusion, anesthesia flow control and urinary catheters. During such medical interventions, typically a number of channels is consecutively used per patient. The fluid flow meter disclosed in U.S. Pat. No. 5,533,412 is too costly to be disposed every time the channel is replaced. Recycling of the fluid flow meter disclosed in U.S. Pat. No. 5,533,412 is not an economically feasible option either, given the efforts that will be required to employ the fluid flow meter for another channel.

SUMMARY OF THE INVENTION

It is a first object of the invention to provide a sensor for measuring a velocity in applications in which a channel is regularly replaced, particularly sterile medical applications.

It is a second object of the invention to provide a control unit for cooperation with the sensor.

It is a third object of the invention to provide a system comprising the sensor and the channel.

It is a fourth object of the invention third object of the invention to provide a method for the controlled delivery of a liquid medication in applications in which the channel is regularly exchanged.

The first object of the invention is achieved by the sensor according to the invention, which sensor is arranged for measuring a velocity of a fluid, i.e. a liquid or a gas, flowing through a channel, which sensor comprises a chip and a sensor receiver, which chip comprises a heating element for heating the fluid, and a transducer arrangement for generating a measurement signal indicative for the velocity of the fluid flowing through the channel, which measurement signal is based on the ratio of a first spatial temperature difference and a second spatial temperature difference, and which sensor receiver is arranged for receiving an electromagnetic radiation for powering the heating element.

Through basing the measurement signal on the ratio of a first spatial temperature difference and a second spatial temperature difference, the measurement signal is independent of an actual level of power supplied to the heating element. Namely, the first spatial temperature difference and the second temperature difference both relate to the power dissipated by the heating element in an affine way, at least for a range of fluid flow velocities. An affine relation amounts to a linear relation provided the constant term of the linear expression equals zero. Therefore, by taking the ratio the first spatial temperature difference and the second temperature difference, a relation is obtained which is independent of the power dissipated by the heating element. Through relating the measurement signal to this relation, the measurement signal is robust regarding disturbances with regard to the amount of power dissipated by the heating element.

Apart from disturbances such as variations in the electrical resistance of the heating element and manufacturing tolerances regarding the chip comprised in the sensor, techniques which provide power via electromagnetic radiation may be subject to significant disturbances on the amount of power supplied to and dissipated by the heating element. For instance, the position of the sensor receiver with regard to a transmitting device may vary under the influence of mechanical shocks or due replacing the sensor.

The sensor comprises a sensor receiver for receiving an electromagnetic radiation for powering the heating element. Herein the heating element can be powered via the energy contained in the electromagnetic radiation itself. Alternatively, the electromagnetic radiation can be employed to enable an energy storage such as a miniaturized battery, which miniaturized battery powers the heating element in its turn. In both cases, no rectifier and accompanying circuitry to control the voltage level are installed between the sensor receiver and the heating element. Namely, no miniaturized rectifier and accompanying control circuitry are capable of handling the level of power required for powering the heating element. As a consequence, the amount of power dissipated by the heating element cannot be controlled and is therefore likely to fluctuate.

Since the measurement signal is robust regarding disturbances acting on the amount of power dissipated by the heating element, techniques that provide power via electromagnetic radiation have become feasible for application in a sensor for accurately measuring a fluid flow velocity.

Due to the fact that power is provided via electromagnetic radiation, i.e. power is provided wirelessly, the sensor allows for an easy handling due to the absence of bothersome wiring. Further, the sensor allows for a reliable handling and a reliable application since the risk of pollution of electrical contacts, which is inherently present in e.g. medical applications, is rather limited.

Furthermore, the sensor can easily be employed in disposable articles, i.e. the financial loss through disposing the sensor is substantially small. Obviously, the sensor need not necessarily be disposed, i.e. it does allow for a prolonged use. Specifically, in case a channel is replaced, the sensor can be disposed along with the channel whereas the further circuitry, which is the most expensive part of the overall system, can be reused. Because of that, the sensor particularly allows for an economically attractive employment in applications in which the channel is regularly replaced, particularly sterile medical applications, such as intravenous infusion, anesthesia flow control, urinary catheters, breathing control as well as enteral and parenteral nutrition flow measurement. Because of the sensor's disposability, the extremely labor-intensive process of making the sensor sterile again is effectively circumvented.

Apart from medical applications, the sensor is well suited for measuring fluid flow velocity in applications such as clean water production, chemicals refinery, oil exploitation and diesel engines.

The second object of the invention is achieved by the control unit according to the invention, which control unit is arranged for cooperation with the sensor, which control unit comprises a control transmitter for transmitting the electromagnetic radiation to the sensor receiver. By comprising the control transmitter, the control unit is capable of supplying the electromagnetic radiation for powering the heating element. As a result, the cooperation between the sensor and the control unit is realized without a physical connection. The latter quality guarantees an economically attractive employment in applications in which the channel is regularly replaced because the sensor is easily disconnectable from the control unit, which control unit can be reused whereas the sensor is allowed to be disposed.

The third object of the invention is achieved by the system according to the invention, which system comprises both the sensor according to the invention and the control unit according to the invention.

The fourth object of the invention is achieved by a method according to the invention, which method is arranged for controlled delivery of a liquid medication, comprising the step of establishing a predefined flow velocity, the step of detachably connecting the control unit to the channel, the step of controlled delivery of the liquid medication through the channel by application of the sensor and the actuator, the step of disconnecting the control unit from the channel and the step of disposing the channel. The step in which the control unit and the channel are being separated from one another, i.e. the channel is disposed whereas the control unit is reused, guarantees an economically attractive employment of the method in applications in which the channel is regularly exchanged.

In an embodiment of the sensor according to the invention, the first spatial temperature difference is the numerical difference between the temperature of the fluid prior to the heating element and the temperature of the fluid after the heating element, and the second spatial temperature difference is the numerical difference between temperatures of the fluid at locations upstream of the heating element added to the numerical difference between temperatures of the fluid at locations downstream of the heating element. The benefit of this embodiment is in its symmetric configuration with respect to the heating element. As a result, this embodiment does not presume a specific orientation with regard to the flow direction.

In a further embodiment of the sensor according to the invention, the sensor receiver is implemented by an antenna, in which antenna the heating element is integrated.

In both cases, no rectifier and accompanying circuitry to control the voltage level are installed between the sensor receiver and the heating element. Namely, no miniaturized rectifier and accompanying control circuitry are capable of handling the level of power required for powering the heating element. As a consequence, the amount of power dissipated by the heating element cannot be controlled and is therefore likely to fluctuate.

In a further embodiment of the sensor according to the invention, the sensor is situated in or at a wall of the channel. As a result, the sensor can be installed in a relatively close proximity of the fluid flowing through the channel as to reduce the thermal resistance between the fluid and the flow sensor with the purpose of increasing the level of accuracy for the measurement signal. Through integrating the sensor with the wall of the channel, the sensor does not physically contact the fluid. The latter quality is essential for medical applications such as intravenous infusion or urinary catheter flow control. Namely, in these applications it is utterly important to prevent the emergency situation in which the sensor or its parts are released and are subsequently being carried towards the human or animal body by the fluid flow.

In a further embodiment of the sensor according to the invention, the sensor is arranged substantially co-axially with the channel. In this text, co-axially is to be interpreted as an arrangement of bodies or surfaces sharing a common axis in an axial direction. Hence, circular as well as non circular bodies and surfaces allow for a co-axial arrangement. Through arranging the sensor and the channel substantially co-axially, the accuracy of the measurement signal generated by the transducer arrangement is increased.

In a further embodiment of the sensor according to the invention, the chip comprises a sensor transmitter for transmitting the measurement signal. As a result, the sensor is physically entirely disconnected from any circuitry that drives the sensor and responds to the measurement signal generated by the transducer arrangement comprised in the sensor.

In a further embodiment of the control unit according to the invention, the control unit comprises an actuator for controlling the flow velocity of the fluid flowing through the channel. Consequently, the dependence of the flow velocity on external circumstances such as gravity is circumvented.

In a further embodiment of the control unit according to the invention, the control unit is provided with a facility for detachably connecting the control unit to the channel. Because of that, the control unit and the actuator comprised therein are capable of controlling the velocity of the fluid in the channel without impeding the disposability of the sensor and the channel. This quality is of particular benefit for medical applications wherein the channel comprising the sensor is regularly replaced, typically once a day. Namely, by detachably connecting the channel and the control unit, the channel allows for disposition whereas the control unit can be reused. Obviously, the absence of wiring largely facilitates a replacement of the channel containing the sensor.

In a further embodiment of the control unit according to the invention, the actuator is controllable by a signal relating to a deviation between the predefined flow velocity and the measurement signal generated by the transducer arrangement comprised in the sensor. As a result, no intervention of e.g. a doctor or a paramedic is required to adjust a setting of the actuator on the basis of a value of the measurement signal in order to bring the fluid flow in conformity with a predefined medication regime.

In a further embodiment of the control unit according to the invention, the actuator comprises an actuator receiver for receiving the measurement signal generated by the transducer arrangement comprised in the sensor. Because of that, the sensor and the actuator are operable without having any hardware connection.

DETAILED DESCRIPTION OF THE EMBODIMENTS

Figure 1:
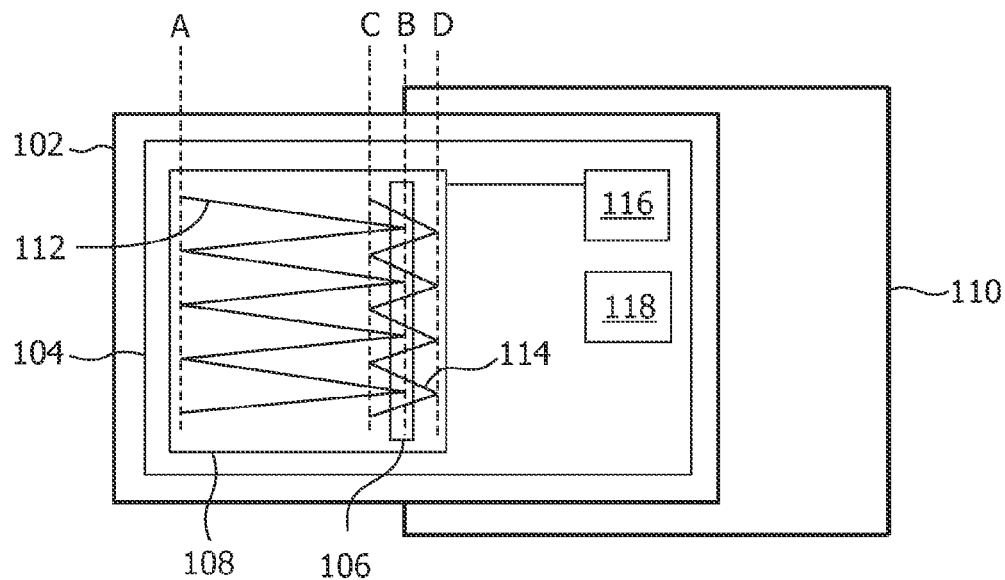
FIG. 1 schematically displays a first embodiment of the system according to the invention, wherein the sensor comprises a transducer arrangement build up of two thermopiles.

FIG. 1 displays a sensor 102 comprising a chip 104 which has a substrate manufactured from poly-imide. The benefit of the latter materials is in their relatively low RF power loss. Here RF refers to Radio Frequency, which implies a frequency ranging from approximately 1 MHz up to about 10 GHz. The sensor 102 further comprises an antenna 110 for receiving an electromagnetic radiation. The energy contained in the electromagnetic radiation is employed for powering a heating element 106, which heating element 106 is arranged for heating a fluid. The heating element 106 is integrated with the antenna 110 through locally providing a relatively large electrical resistance to the antenna 110. The antenna 110 is locally provided with a material having a higher electrical resistance or alternatively, the antenna 110 is locally provided with a smaller cross-sectional area. Consequently, power will be dissipated along the relatively large electrical resistance, which dissipation will result in heating. The antenna 110, at least its part which is not arranged for heating the fluid, is not situated on the chip 104.

The chip 104 comprises a transducer arrangement 108, which transducer arrangement 108 comprises a first thermopile 112 and a second thermopile 114. In this text, a thermopile refers to a series connection of a plurality of thermocouples. A thermopile produces an output relating to a local temperature gradient or temperature difference rather than measuring an absolute temperature. The first thermopile 112 registers the difference between the temperatures at line A and at line B. Hence, the first thermopile 112 measures the difference between the temperature of the heating element 106 and the temperature at a reference position, which temperature is further referred to as the reference temperature. Likewise, the second thermopile 114 measures the difference between the temperatures at line C and at line D. Therefore, the second thermopile 114 measures the difference between the temperature of the fluid after passing the heating element 106 and the temperature of the fluid prior to passing the heating element 106. The transducer arrangement 108 is arranged for generating a measurement signal indicative for a velocity of a fluid flowing through a channel based on the outputs of the first thermopile 112 and the second thermopile 114. The chip further comprises a sensor transmitter 116 for transmitting the measurement signal generated by the transducer arrangement 108. Furthermore, the chip comprises a memory 118. In the memory 118 data are stored, which data can contain the calibration qualities of the channel through which the fluid from which the velocity is to be measured by the sensor 102 is flowing. The employment of the sensor 102 in cooperation with a channel is disclosed in FIG. 2, which figure relates to the second embodiment of the sensor according to the invention.

Figure 3:
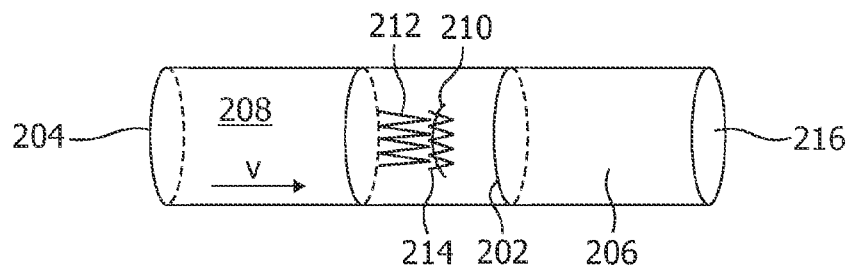
FIG. 3 schematically displays a third embodiment of the system according to the invention, wherein an electromagnetic radiation received by a sensor receiver enables a battery for powering a heating element.
Figure 4:
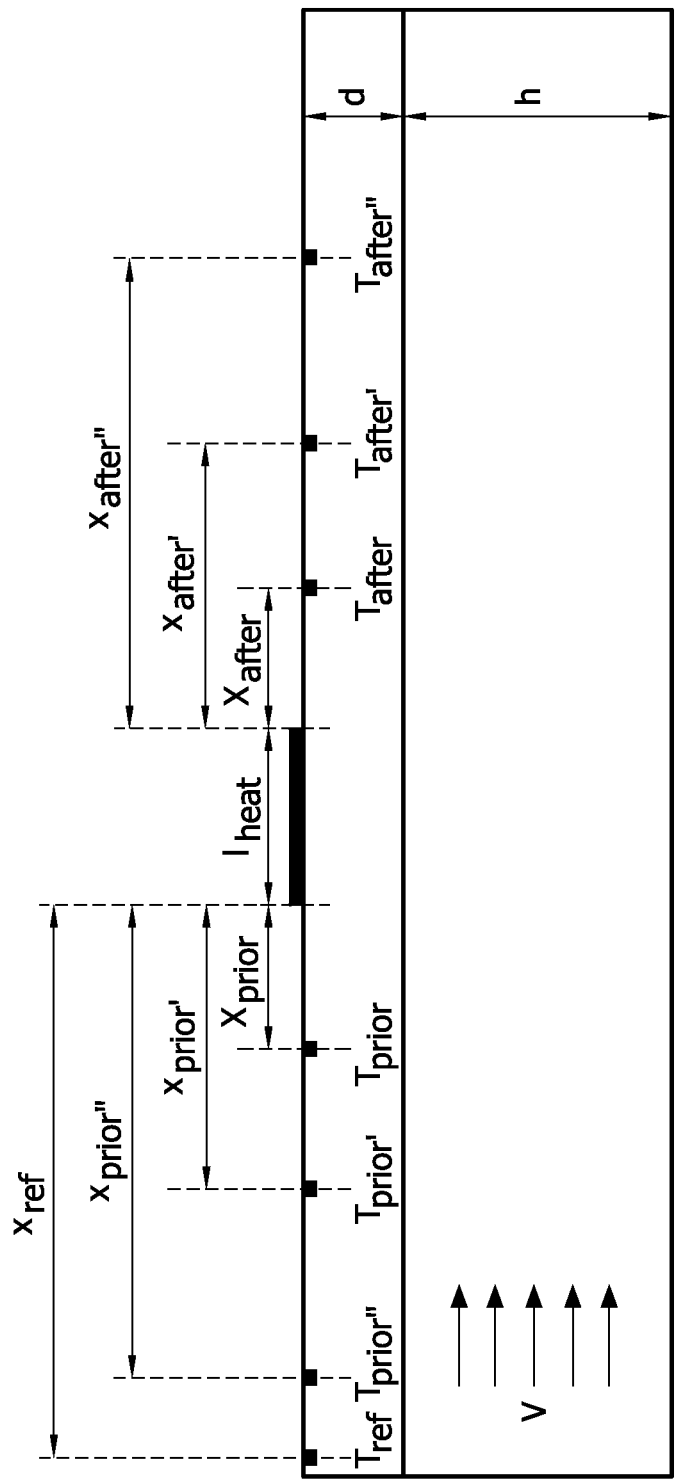
FIG. 4 schematically provides an explanation for the quantities measurable by the transducer arrangements comprised in the first embodiment and the third embodiment of the sensor according to the invention.

FIG. 3 displays an embodiment of the sensor according to the invention wherein the sensor 202 is situated at a wall 204 of a channel 206 for measuring a velocity v [m/s] of a fluid 208 flowing through the channel 206. A heating element 210 is arranged for heating the fluid 208. A first thermopile 212 is arranged for measuring the difference between the temperature $T_{heat}$ [K] of the heating element 210 and a reference temperature $T_{ref}$ which is registered at a distance $x_{ref}$, see FIG. 4, downstream from the heating element 210. The output of the first thermopile 212, i.e. $T_{heat}-T_{ref}$, relates to the power P [W] supplied to the heating element 210 and the flow velocity v of the fluid 208 in the channel 206 according to the following relationship:

$$T_{heat} - T_{ref} = T_0 \cdot (1 - e^{-\alpha_1 x_{ref}}), \qquad [\text{I}]$$

wherein:

$$T_0 = \frac{P}{\lambda_{fl} b_{heat} \left( \frac{l_{heat}}{h} + \sqrt{\frac{v^2 h^2}{4 a_{fl}} + 4\kappa} \right)}, \qquad [\text{II}]$$

$$\alpha_1 = \frac{v + \sqrt{v^2 + 16 a_{fl}^2 \kappa / h^2}}{4 a_{fl} \kappa}, \qquad [\text{III}]$$

$$\kappa = \frac{1}{2} + \frac{\lambda_{wall} d}{\lambda_{fl} h} \qquad [\text{IV}]$$

and wherein $l_{heat}$ denotes the length of the heater, d is the distance from the sensor 202 to the fluid 208, h is the height of the flow channel, see FIG. 4 wherein a graphical explanation is given for the aforementioned quantities. Further, $b_{heat}$ is the width of the heating element 210, $a_{fl}$ is the thermal diffusivity of the fluid 208, $\lambda_{fl}$ is the thermal conductivity of the fluid 208 and $\lambda_{wall}$ is the thermal conductivity of the wall 204, i.e. the thermal conductivity of the material in between the sensor 202 and the fluid 208.

A second thermopile 214 is arranged for measuring the difference between the temperature Tafter of the fluid 208 after passing the heating element 210 and the temperature Tprior [K] of the fluid 208 prior to passing the heating element 210. The output of the first thermopile 212, i.e. $T_{after}-T_{prior}$, relates to the velocity v of the fluid 208 in the channel 206 and the temperature $T_0$ according to the following relationship:

$$T_{after} - T_{prior} = T_0 \cdot (e^{\alpha_2 x_{prior}} - e^{-\alpha_1 x_{after}}), \qquad [\text{V}]$$

wherein:

$$\alpha_2 = \frac{v - \sqrt{v^2 + 16 a_{fl}^2 \kappa / h^2}}{4 a_{fl} \kappa}, \qquad [\text{VI}]$$

and wherein $x_{prior}$ and $x_{after}$ respectively denote the downstream distance and the upstream distance from the heating element 110 to the locations at which $T_{prior}$ and $T_{after}$ are being registered by the second thermopile 214, see FIG. 4.

The measurement signal generated by the transducer arrangement (not shown) comprised in the sensor 202 is based on the ratio τ of the output of the first thermopile 212 and the output of the second thermopile 214. Provided P≠0, the measurement signal τ follows from the following dimensionless relationship:

$$\tau = \frac{T_{after} - T_{prior}}{T_{heat} - T_{ref}} = \frac{e^{\alpha_2 x_{after}} - e^{-\alpha_1 x_{prior}}}{1 - e^{-\alpha_1 x_{ref}}}, \qquad [\text{VII}]$$

wherein $\alpha_1$ and $\alpha_2$ follow from equations [III] and [VI], respectively. The ratio τ is independent of the power P dissipated by the heating element 210. Hence, the measurement signal is robust regarding disturbances acting on the power dissipated by the heating element 210. Furthermore, the measurement signal according to relationship [V] is invariant under variations in an ambient temperature. Hence, it has no offset regarding temperature. Furthermore, the measurement signal is sensitive to a substantially large range of the velocity v of the fluid 208 flowing through the channel 206. As a result, the measurement signal provides a relatively large range in which it is indicative for the velocity v.

The sensor 202 is calibrated by measuring the ratio τ for a range of velocities and storing the calibration by means of a look-up table in a memory (not shown) comprised in the sensor 202. On the basis of the calibration, the velocity v can be determined during use by measuring τ and by subsequently employing the look-up table. Alternatively, the velocity v can be computed on the basis of [V] by measuring the ratio τ and by subsequently employing an iterative scheme, e.g. the Newton-Raphson method or the bisection method, which imply the computation of v for which the equation $\tau - (e^{\alpha_2 x_{after}} - e^{-\alpha_1 x_{prior}})/(1 - e^{-\alpha_1 x_{ref}})$ equals zero. An advantage of the latter approach is in the fact that modifications in e.g. fluid properties can be accounted for.

In equations [I] to [V], the velocity v is presumed to have a uniform profile across a cross-sectional area 216 of the flow channel 206. However, for a laminar flow regime a parabolic velocity profile will be obtained. Within a relatively large range of flow velocities, the uniform velocity profile can be unambiguously related to the parabolic velocity profile. Therefore, the discrepancy mentioned before imposes no limitation regarding the accuracy of the sensor 202.

Figure 2:
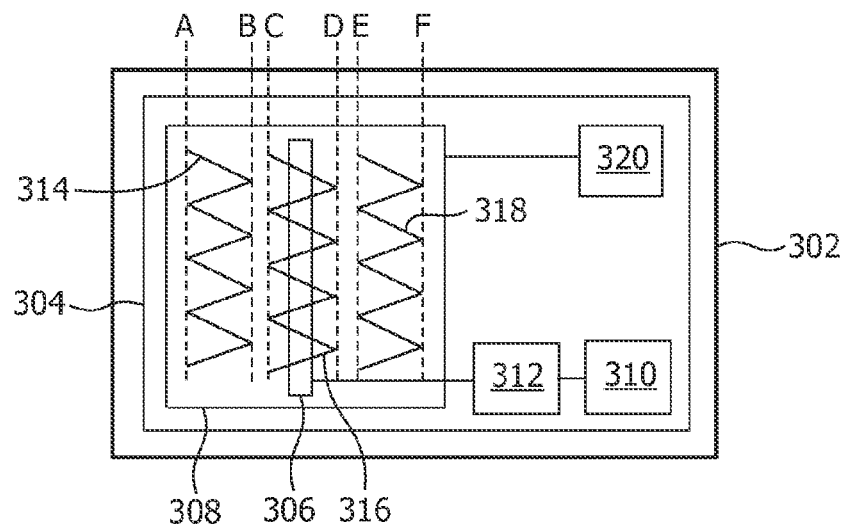
FIG. 2 schematically depicts a second embodiment of the sensor according to the invention, wherein the sensor is situated in the wall of a channel.

FIG. 2 displays a sensor 302 comprising a chip 304 which has a substrate manufactured from poly-imides, and a sensor receiver 310. The sensor receiver 310 is arranged for receiving an electromagnetic radiation. The chip 304 comprises a heating element 306 and a transducer arrangement 308. Here, an energy contained in the electromagnetic radiation is employed for enabling a preferably miniaturized battery 312. The energy stored in the battery 312 is employed for powering the heating element 306. The transducer arrangement 308 comprises a first thermopile 314, a second thermopile 316 and a third thermopile 318.

The first thermopile 314 registers the numerical difference between the temperatures at line A and at line B. Hence, the first thermopile 314 measures the difference between the temperatures of the fluid at two locations prior to the heating element 306. Likewise, the second thermopile 114 measures the difference between the temperatures at line C and at line D. Therefore, the second thermopile 114 measures the difference between the temperature of the fluid after passing the heating element 106 and the temperature of the fluid prior to passing the heating element 106. The third thermopile 318 registers the numerical difference between the temperatures at line E and at line F. Hence, the third thermopile 318 measures the difference between the temperatures of the fluid at two locations after the heating element 306. The transducer arrangement 308 is arranged for generating a measurement signal indicative for a velocity of a fluid flowing through a channel based on the outputs of the first thermopile 314, the second thermopile 316 and the third thermopile 318. The chip 304 further comprises a sensor transmitter 320 for transmitting the measurement signal generated by the transducer arrangement 308. The employment of the sensor 302 in cooperation with a channel through which the fluid from which the velocity is to be measured by the sensor 302 is flowing is disclosed in FIG. 5, which figure relates to the fourth embodiment of the sensor according to the invention.

Figure 5:
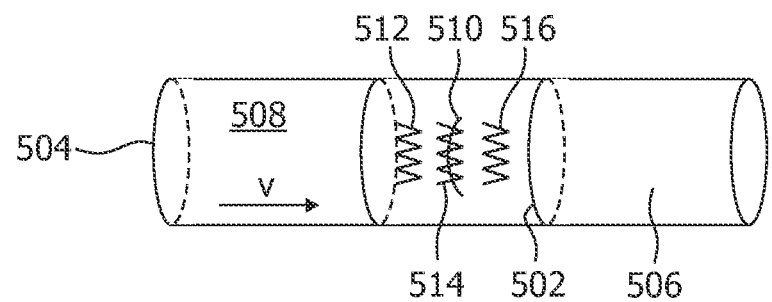
FIG. 5 schematically depicts a fourth embodiment of the sensor according to the invention, wherein the sensor is situated in the wall of a channel and wherein the sensor comprises a transducer arrangement build up of three thermopiles.

FIG. 5 displays an embodiment of the sensor according to the invention wherein the sensor 502 is situated at a wall 504 of a channel 506 for measuring a velocity v [m/s] of a fluid 508 flowing through the channel 506. A heating element 510 is arranged for heating the fluid 508.

A first thermopile 512 is arranged for measuring the difference between the temperatures $T_{prior'}$ [K] and $T_{prior''}$ [K] of the fluid 508 at two locations downstream of the heating element 510. The output of the first thermopile 512, i.e. $T_{prior'} - T_{prior''}$ relates to the velocity V of the fluid 508 in the channel 506 and the temperature $T_0$ according to the following relationship:

$$T_{prior'} - T_{prior''} = T_0 (e^{\alpha_1 x_{prior'}} - e^{\alpha_1 x_{prior''}}) \qquad [\text{VIII}],$$

wherein $T_o$ follows from equation [II], and wherein $\alpha_1$ follows from equation [III].

A second thermopile 514 is arranged for measuring the difference between the temperature $T_{after}$ of the fluid 508 after passing the heating element 510 and the temperature $T_{prior}$ [K] of the fluid 508 prior to passing the heating element 210. The output of the second thermopile 514, i.e. $T_{after} - T_{prior}$, relates to the velocity v of the fluid 208 in the channel 206 and the temperature $T_0$ according to equation [V].

A third thermopile 516 is arranged for measuring the difference between the temperatures $T_{after'}$ [K] and $T_{after''}$ [K] of the fluid 508 at two locations upstream of the heating element 510. The output of the third thermopile 516, i.e. $T_{after'} - T_{after''}$, relates to the velocity v of the fluid 508 in the channel 506 and the temperature $T_0$ according to the following relationship:

$$T_{after'} - T_{after''} = T_0 \cdot (e^{\alpha_2 x_{after'}} - e^{-\alpha_2 x_{after''}}) \qquad [\text{IX}]$$

wherein $T_o$ follows from equation [II], and wherein $\alpha_2$ follows from equation [VI].

The measurement signal generated by the transducer arrangement (not shown) comprised in the sensor 502 is based on the ratio τ' of the outputs of the first thermopile 512, the second thermopile 514 and the third thermopile 516. Provided P≠0, the measurement signal τ' follows from the following dimensionless relationship:

$$\tau' = \frac{T_{after} - T_{prior}}{(T_{prior'} - T_{prior''}) + (T_{after'} - T_{after''})} \qquad [\text{X}]$$

$$= \frac{e^{\alpha_2 x_{after}} - e^{-\alpha_1 x_{prior}}}{(e^{\alpha_1 x_{prior'}} - e^{-\alpha_1 x_{prior''}}) + (e^{\alpha_2 x_{after'}} - e^{-\alpha_2 x_{after''}})}$$

wherein $\alpha_1$ and $\alpha_2$ follow from equations [III] and [VI], respectively. The ratio τ' is independent of the power P dissipated by the heating element 510. Hence, the measurement signal is robust regarding disturbances acting on the power dissipated by the heating element 510. Furthermore, the measurement signal according to relationship [V] is invariant under variations in an ambient temperature. Hence, it has no offset regarding temperature. Furthermore, the measurement signal is sensitive to a substantially large range of the velocity v of the fluid 508 flowing through the channel 506. As a result, the measurement signal provides a relatively large range in which it is indicative for the velocity v.

Figure 6:
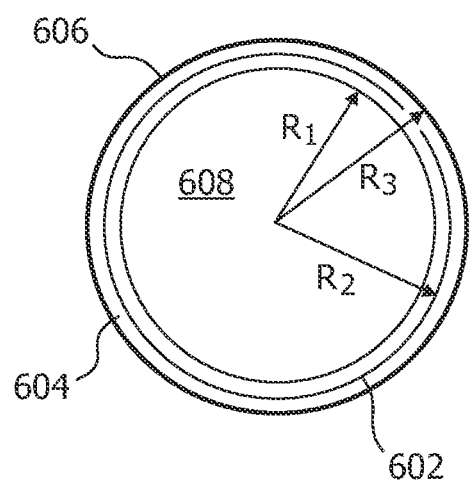
FIG. 6 schematically shows a cross-sectional view of a fifth embodiment of the sensor according to the invention, wherein the sensor is aligned co-axially with the channel.

FIG. 6 displays a preferred embodiment wherein the sensor 602 is situated in a wall 604 of the channel 606, for measuring a velocity of the fluid 608 flowing through the channel 606. The wall 604 of the channel 606 is made of a suitable plastic such as poly-imide. The channel 606 has an inner radius $R_1$ and an outer radius $R_2$. The sensor 602 is arranged co-axially with the channel 606 at a radius $R_3$ for which it holds that $R_1 < R_2 \leq R_3$. Preferably, to reduce the thermal resistance between the fluid and the flow sensor with the purpose of increasing the level of accuracy for the measurement signal generated by the transducer arrangement (not shown) comprised in the sensor 602, the distance $R_2 - R_1$ is relatively small, e.g. at about 60 μm. Clearly, the sensor 602 does not physically contact the fluid 608 flowing through the channel 606. Preferably, the sensor 602 envelops the fluid 608 to a relatively large extend in order to increase an accuracy of a measurement signal generated by a transducer arrangement (not shown) comprised in the sensor 602.

Figure 7:
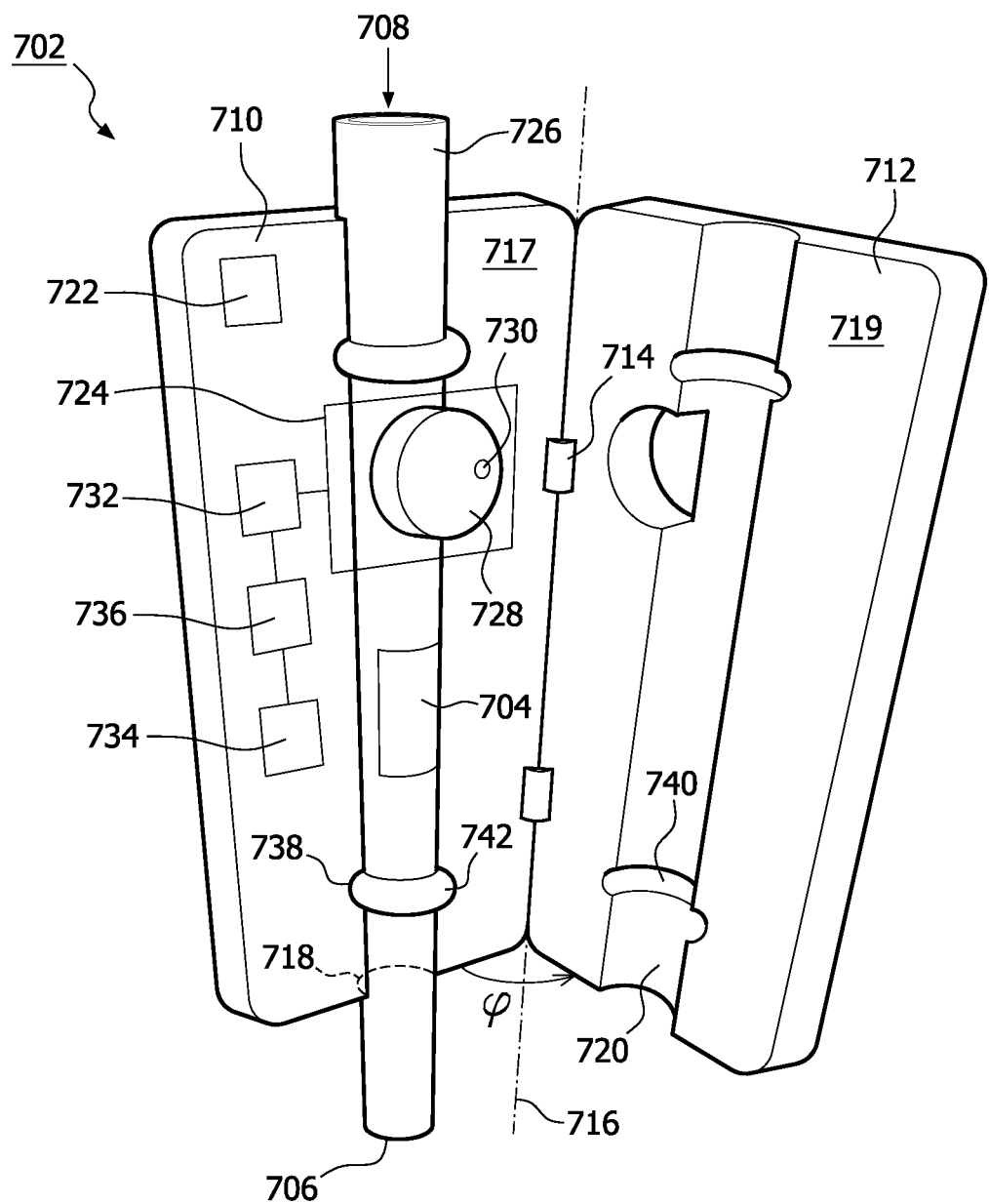
FIG. 7 schematically shows an embodiment of the system according to the invention, wherein the control unit according to the invention is arranged for cooperation with the sensor according to the invention.

FIG. 7 displays an embodiment of the system according to the invention. The system comprises a control unit 702 and a sensor 704. The sensor is situated in a wall 706 of a channel 708. The control unit 702 is arranged for cooperation with the sensor 704. The control unit 702 comprises a first body 710 and a second body 712. In this embodiment, both bodies are elongated bodies. In this embodiment, the first body 710 and the second body 712 are connected via a hinge arrangement 714. Hence, the first body 710, the second body 714 and the hinge arrangement constitute a casing. Alternatively, the first and the second body may be connectable by means of screws, snap fasteners or clamps.

The hinge arrangement 714 establishes a mutual rotational degree of freedom $\phi$ along an axis of rotation 716 for the first body 710 and the second body 712. The first body 710 comprises a first face 717 having a first cavity 718 whereas the second body comprises a second face 719 having a second cavity 720. In case the mutual rotational degree of freedom $\phi$ vanishes, i.e. the faces 717 and 719 meet each other hence the casing is closed, a constitution of the first cavity 718 and the second cavity 720 is capable of encasing the channel 708.

The control unit 702 comprises a control transmitter 722 for transmitting an electromagnetic radiation to the sensor receiver (not shown) comprised in the sensor 704 for powering the heating element (not shown) comprised in the sensor 704. Herein, the heating element is powered via an energy contained in the electromagnetic radiation itself. Alternatively, the electromagnetic radiation can be employed to enable the energy storage such as a miniaturized battery (not shown) comprised in the sensor, which miniaturized battery powers the heating element in its turn.

The control unit 702 furthermore comprises a control actuator 724 for controlling the flow velocity of the fluid 726 flowing through the channel 708. Consequently, a dependence of the flow velocity on external circumstances such as gravity is prevented from. The actuator 724 is implemented by a preferably cylindrical body 728 which is eccentrically rotatable around a pivot 730 by an electromagnetic motor 732. The electromagnetic motor 732 is controllable by a signal relating to a deviation between the predefined flow velocity of the fluid 726 in the channel 708 and the velocity indicated by a measurement signal generated by a transducer arrangement (not shown) in the sensor 704. Hence no intervention of e.g. a doctor or a paramedic is required to adjust a setting of the actuator 724 in order to bring the velocity of the fluid 726 in the channel 708 in conformity with a predefined medication regime. The actuator 724 comprises an actuator receiver 734 for receiving the measurement signal generated by the transducer arrangement comprised in the sensor 704. A comparator 736 compares the measurement signal received by the actuator receiver 734 to a predefined reference value for the velocity of the fluid 726 in the channel 708, which reference value is grounded on a predetermined medication regime.

By appropriately encasing the channel 708 through vanishing of the rotational degree of freedom $\phi$ along the axis of mutual rotation 716, the eccentrically rotatable body 718 contained in the actuator 724 is able to control a size of a cross-section of the channel 708. With that, the flow velocity v of the fluid 726 in the channel 708 is effectively controlled.

The first cavity 718 comprises a first plurality of circular hollows 738. The first plurality of circular hollows 738 has a non-parallel orientation compared to the first cavity 718. Likewise, the second cavity 720 comprises a second plurality of circular hollows 740. The second plurality of circular hollows 740 has an orientation matching to the orientation of the first plurality of circular hollows 738. The first plurality of circular hollows 738 and the second plurality of circular hollows 740 are arranged for encasing a plurality of bulges 742 mounted on the channel 708. By appropriately encasing the channel 708 through vanishing of the rotational degree of freedom $\phi$ along the axis of mutual rotation 716, and by aligning the plurality of bulges 742 with the first plurality of circular hollows 738 and the second plurality of circular hollows 740, a mutual axial position of the channel 708 and the control unit 702 is established.

The system comprising the control unit 702 and the sensor 704 may be integrated into a system that stores, displays and analyzes information regarding the velocity of the fluid 726 flowing through the channel 708.

An example of such a system may be a patient monitoring system. In a patient monitoring system, several devices measure vital signs such as a patient's blood pressure and heartrate and transmit them to a monitoring device. The monitoring device stores information regarding the vital signs and analyses and displays this information, for instance upon request by a medical professional. The information provided by the sensor 704 regarding the velocity of the fluid 726 flowing through the channel 708 may be essential to be monitored by the patient monitoring system, e.g. in applications such as intravenous infusion. For this purpose, the control unit is employed with a further control transmitter 744, which preferably provides a wireless connection to the patient monitoring system.

It is stressed the application of the sensor 704 allows for application in conjunction with a range of pumps, medical gravity drips or disposable pump systems, possibly manufactured by various companies. Because of that, the sensor 704 can act as a standard interface between fluid transportation systems and the patient monitoring system aforementioned.

Figure 8:
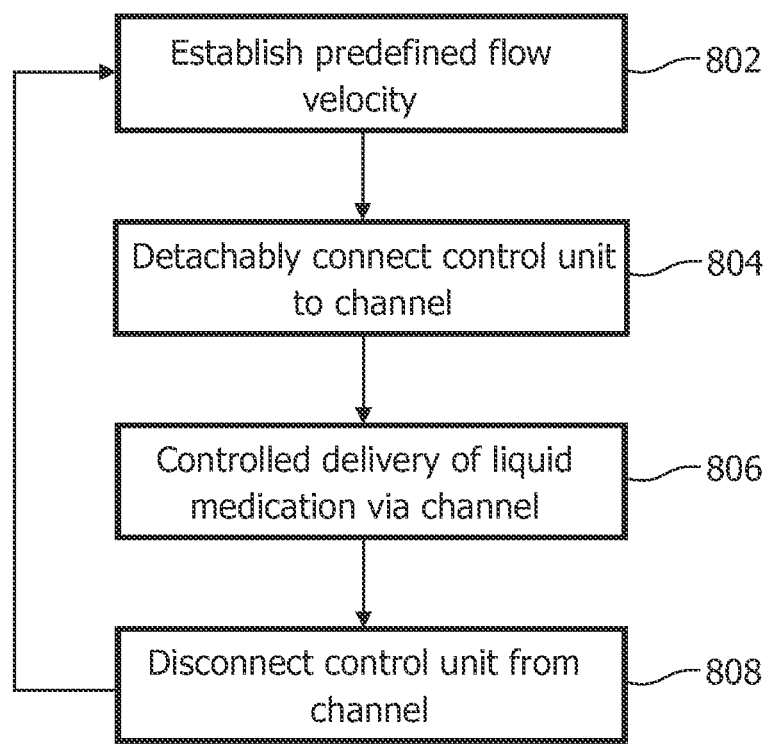
FIG. 8 schematically displays a flowchart representing an embodiment of the method according to the invention wherein control unit is being reused.

FIG. 8 displays a flowchart representing an embodiment of the method according to the invention. The method is arranged for delivery of a liquid medication, particularly intravenous delivery of a liquid medication under sterile conditions. A step 802 comprises establishing a predefined value for the velocity v based on a specific therapeutic regime. A step 804 comprises detachably connecting the control unit in conformity with the embodiment of the system according to the invention to a channel, which channel contains in its wall the sensor pursuant to the first embodiment of the sensor according to the invention. A step 806 comprises controlled delivery of a liquid medication by controlling the control actuator comprised in the control unit on the basis of a signal relating to a deviation between the predefined level for the velocity and a velocity indicated by a measurement signal generated by a transducer arrangement comprised in the sensor. A step 808 comprises disconnecting the control unit from the channel. The step of establishing a predefined value for the velocity v can be carried out multiple times, i.e. for instance during the delivery of the fluid.

While the invention has been illustrated and described in detail in the drawings and in the foregoing description, the illustrations and the description are to be considered illustrative or exemplary and not restrictive. The invention is not limited to the disclosed embodiments. It is noted that the sensor and the control unit according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A sensor (102) for measuring a velocity of a fluid (208) flowing through a channel (206), the sensor comprising:
   a chip (104) and a sensor receiver (310),
      wherein the chip includes
         a heating element (106) for heating the fluid, and
         a transducer arrangement (108) spatially positioned on the chip across the heating element for generating a measurement signal indicative for the velocity of the fluid flowing through the channel based on the ratio of a first spatial temperature difference and a second spatial temperature difference, and
      wherein the sensor receiver is arranged for receiving an electromagnetic radiation for powering the heating element.

2. The sensor according to claim 1, wherein the first spatial temperature difference is the numerical difference between the temperature of the fluid prior to the heating element and the temperature of the fluid after the heating element, and the second spatial temperature difference is the numerical difference between temperatures of the fluid at locations prior to the heating element added to the numerical difference between temperatures of the fluid at locations after the heating element.

3. The sensor according to claim 1, wherein the sensor receiver is an antenna (110), wherein the heating element is integrated with the antenna.

4. The sensor according to claim 1, wherein the chip further includes a sensor transmitter (116) for transmitting the measurement signal.

5. The sensor according to claim 1, wherein the sensor is situated in or at a wall of the channel.

6. The sensor according to claim 5, wherein the sensor is arranged substantially coaxially with the channel.

7. The sensor according to claim 1, wherein the chip further includes a memory (118) for storing data.

8. The sensor according to claim 1, wherein the first spatial temperature difference is the numerical difference between the temperature of the fluid prior to the heating element and the temperature of the fluid after the heating element, and the second spatial temperature difference is the numerical difference between temperatures of the fluid at the heating element and at a reference location.

9. A control unit (602) for cooperation with a sensor (102) for measuring a velocity of a fluid (208) flowing through a channel (206), wherein the sensor includes a chip (104) and a sensor receiver (310),
   wherein the chip includes
      a heating element (106) for heating the fluid, and
      a transducer arrangement (108) spatially positioned on the chip across the heating element for generating a measurement signal indicative for the velocity of the fluid flowing through the channel based on the ratio of a first spatial temperature difference and a second spatial temperature difference, and
   wherein the sensor receiver is arranged for receiving an electromagnetic radiation for powering the heating element,
   the control unit comprising:
      a control transmitter (626) for transmitting the electromagnetic radiation to the sensor receiver.

10. The control unit according to claim 9, wherein the control unit further includes a facility for detachably connecting the control unit to the channel.

11. The control unit according to claim 9, wherein the control unit further includes a control actuator (624) for controlling the flow velocity of the fluid flowing through the channel.

12. The control unit according to claim 11, wherein the control actuator is controllable by a signal relating to a deviation between a predefined flow velocity and the velocity indicated by the measurement signal generated by the transducer arrangement comprised in the sensor.

13. The control unit according to claim 12, wherein the actuator comprises an actuator receiver (534) for receiving the measurement signal generated by the transducer arrangement comprised in the sensor.

14. A system comprising;
   a sensor (102) for measuring a velocity of a fluid (208) flowing through a channel (206), wherein the sensor includes a chip (104) and a sensor receiver (310),
      wherein the chip includes
         a heating element (106) for heating the fluid, and
         a transducer arrangement (108) spatially positioned on the chip across the heating element for generating a measurement signal indicative for the velocity of the fluid flowing through the channel based on the ratio of a first spatial temperature difference and a second spatial temperature difference, and
      wherein the sensor receiver is arranged for receiving an electromagnetic radiation for powering the heating element; and
   the control unit includes a control transmitter (626) for transmitting the electromagnetic radiation to the sensor receiver.

15. The system according to claim 14, wherein a predefined fluid flow velocity is established in accordance with a medical application.

16. The system according to claim 14, wherein the first spatial temperature difference is the numerical difference between the temperature of the fluid prior to the heating element and the temperature of the fluid after the heating element, and the second spatial temperature difference is the numerical difference between temperatures of the fluid at the heating element and at a reference location.

17. The system according to claim 14, wherein the first spatial temperature difference is the numerical difference between the temperature of the fluid prior to the heating element and the temperature of the fluid after the heating element, and the second spatial temperature difference is the numerical difference between temperatures of the fluid at locations prior to the heating element added to the numerical difference between temperatures of the fluid at locations after the heating element.

18. A method for controlled delivery of a liquid medication, comprising:
- a step (802) of establishing a predefined fluid flow velocity;
- a step (804) of detachably connecting a control unit to a channel, the control unit cooperating with a sensor, for measuring a velocity of a fluid (208) flowing through the channel (206),
    - wherein the sensor includes a chip (104) and a sensor receiver (310),
        - wherein the chip (104) includes
            - a heating element (106) for heating the fluid, and
            - a transducer arrangement (108) spatially positioned on the chip across the heating element for generating a measurement signal indicative for the velocity of the fluid flowing through the channel based on a ratio of spatial temperature differences,
        - the sensor receiver being arranged for receiving an electromagnetic radiation for powering the heating element; and
- a step (806) of controlled delivery of the liquid medication through the channel by application of the sensor and an actuator controlling the flow velocity of the fluid flowing through the channel.

19. The method according to claim 18, wherein the first spatial temperature difference is the numerical difference between the temperature of the fluid prior to the heating element and the temperature of the fluid after the heating element, and the second spatial temperature difference is the numerical difference between temperatures of the fluid at the heating element and at a reference location.

20. The method according to claim 18, wherein the first spatial temperature difference is the numerical difference between the temperature of the fluid prior to the heating element and the temperature of the fluid after the heating element, and the second spatial temperature difference is the numerical difference between temperatures of the fluid at locations prior to the heating element added to the numerical difference between temperatures of the fluid at locations after the heating element.

* * * * *